United States Patent
Lin et al.

(10) Patent No.: US 6,545,253 B2
(45) Date of Patent: Apr. 8, 2003

(54) ELECTRICALLY HEATED FLEXIBLE HEATER

(75) Inventors: Zui-Yeh Lin, Taipei (TW); Jin-Su Chang, Taipei (TW); Jai-Cheng Liu, Taipei (TW); Chun-Jung Kuo, Taipei (TW); Shun-Tung Yang, Taipei (TW)

(73) Assignee: King's Metal Fiber Technologies Co., Ltd., Taipei (TW)

( * ) Notice: Subject to any disclaimer, the term of this patent is extended or adjusted under 35 U.S.C. 154(b) by 0 days.

(21) Appl. No.: 09/997,007

(22) Filed: Nov. 30, 2001

(65) Prior Publication Data

US 2003/0006229 A1 Jan. 9, 2003

(30) Foreign Application Priority Data

Jul. 5, 2001 (TW) .................... 90116440 A

(51) Int. Cl.⁷ ................................ H05B 3/54
(52) U.S. Cl. ................................... 219/528
(58) Field of Search ................ 219/528, 549, 219/211, 545, 529, 217, 212, 530

(56) References Cited

U.S. PATENT DOCUMENTS 4,404,460 A * 9/1983 Kerr .......................... 2/69
4,607,154 A * 8/1986 Mills ....................... 174/126.2
5,801,914 A * 9/1998 Thrash ...................... 219/212
5,883,363 A * 3/1999 Motoyoshi et al. ......... 219/529

* cited by examiner

Primary Examiner—Teresa Walberg
Assistant Examiner—Vinod D Patel
(74) Attorney, Agent, or Firm—Troxell Law Office PLLC

(57) ABSTRACT

The present invention provides a heating apparatus which can be implemented as various articles for keeping human body warm, preventing from cold weather, insulating cold air, etc., e.g., warming clothes, electric blankets, hot compress pads, and curtains for insulating cold air. According to the invention, the heating apparatus includes a soft matrix, a metal yarn and a power supply. The metal yarn is integrated with the soft matrix to construct a loop pattern by a textile process, and has a first end line and a second end line. The first end line and the second end line of the metal yarn are detachably connected to the power supply. When the first end line and the second end line of the metal yarn both are connected to power supply, the power supply supplies the metal yarn with electric energy such that the metal yarn transfers the supplied electric energy into heat.

15 Claims, 2 Drawing Sheets

ELECTRICALLY HEATED FLEXIBLE HEATER

FIELD OF THE INVENTION

The present invention relates to a heating apparatus, and more particularly, to a heating apparatus which incorporates a heating line and a soft matrix together. The example of the soft matrix can be a fabric or a matrix formed of a polymer materials, a synthetic resin, a rubber or the like. In daily, the heating apparatus of the invention can be implemented as an article for keeping human body warm, preventing from cold weather, insulating cold air, etc.

BACKGROUND OF THE INVENTION

People living in the temperate and frigid zones certainly experience extremely cold seasons. These people mostly wear heavy clothes to keep their bodies warm under extremely cold environment. However, in fact, heavy clothes take less purpose of keep human boy for these people who act under extremely cold environment. Besides, heavy clothes also limit activity of these people. Therefore, technologies and skills regarding heating apparatuses for keeping human body warm have been developed and improved continuously. A typical heating apparatus utilizes a fabric to wrap up heavy heating coils or heating plates for transferring electronic energy into heat. If people want to make such heating apparatus effective, they have to carry the heating apparatus closely against their bodies to keep warm. Current heating apparatuses, such as electric blankets, hot compress pads and warming seat cushions, are mostly applied in the aforesaid principle. That is, an significant feature of conventional heating apparatuses is that a fabric wraps up heavy heating coils or heating plates.

The related prior arts regarding conventional heating apparatuses using fabric wrapping up the heavy heating coils or the heating plates refer to U.S. Pat. Nos. 6,160,246, 6,111,233 and 5,792,714.

However, there are many disadvantages of the conventional heating apparatus, describing as follows: (1) conventional heating apparatuses are too heavy to carry; (2) conventional heating apparatuses are hard to be manufactured into wearable heating apparatuses; (3) because the conventional heating apparatuses have to be put closely against human bodies, between the heating apparatus and human bodies need one or more thick textile to protect human bodies from getting burned, therefore, that lowers the warming efficiency of the conventional heating apparatuses; (4) the heavy heating coils or heating plates in the conventional heating apparatuses are not soft enough to attach closely with the human bodies, therefore, that lowers the warming efficiency of the conventional heating apparatuses; (5) the power supply of the conventional heating apparatuses mostly utilize AC current with high power as power supply, therefore, the conventional heating apparatuses are dangerous to the aged users, cardiac, expectant mothers and children; (6) the conventional heating apparatuses mostly consume a large quantity of power, therefore, misusing of the conventional heating apparatuses often causes accidents; (7) the conventional heating apparatuses can not be folded, otherwise the folded heating coils or heating plates will induce local overheat to burn out the wrapping fabric and cause fire; (8) the materials of heating coils or heating plates easily degrade as time goes by, thus the heating coils or heating plates gradually turn hard, brittle and oxidized, therefore, the hard, brittle and oxidized heating coils or heating plates would crack under improper carry, and further, the cracked heating coils or heating plates would discharge accidentally when being used; and (9) the conventional heating apparatuses are mostly not water-resistant, therefore, the conventional heating apparatuses cannot be washed. Obviously, the conventional heating apparatuses with heating coils or heating plates suffers from low efficiency for keeping warm, limited application fields, and unsafety.

Accordingly, an objective of the invention is to provide a heating apparatus. In particular, the heating apparatus according to the invention utilizes metal yarns instead of heavy heating coils or heating plates. Thereby, the heating apparatus according to the invention can be applied in various articles for keeping human body warm, preventing from cold weather, insulating cold air, etc., e.g., warming clothes, electric blankets, hot compress pads, and curtains for insulating cold air.

In addition, recently some clothes on which some phase change materials are coated have been developed to increase wearing comfortability. The phase change materials on the clothes can absorb/release heat to adjust slightly the body temperature of the person wearing the clothes. Some prior arts regarding the clothes coating with phase change materials are disclosed in the following patents: U.S. Pat. Nos. 6,207,738 and 5,885,475. However, the phase change materials coated on the clothes absorb/release a small quantity of heat, and thus can adjust temperature only in a range of about ±2° C. Moreover, the clothes coating with phase change materials can not provide wearers with function of adjusting temperature as their will. Therefore, in fact, the clothes coating with phase change materials can just make wearers comfortable, but can not keep wearers warm. Besides, the cost of the clothes coating with phase change materials is relatively high. Although the clothes coating with phase change material can be washed, the number of washing times regarding the clothes coating with phase change materials is limited. Obviously, so far there is still no wearable heating apparatus with well warming efficiency, low cost, adjustable temperature range as wearers' will, convenience of washing as wearers wish.

Accordingly, another objective of the invention is to provide a wearable heating apparatus. In particular, the wearable heating apparatus according to the invention satisfies all needs mentioned above.

SUMMARY OF THE INVENTION

It is, therefore, an objective of the invention to provide a heating apparatus. Moreover, in particular, the heating apparatus according to the invention utilizes metal yarns instead of heavy heating coils or heating plates. Thereby, the heating apparatus according to the invention can be implemented as various articles for keeping human body warm, preventing from cold weather, insulating cold air, etc., for example, warming clothes, electric blankets, hot compress pads, and curtains for insulating cold air.

It is, therefore, another objective of the invention to provide a wearable heating apparatus. Moreover, in particular, the wearable heating apparatus according to the invention has well heating efficiency, low cost, adjustable temperature range as wearers' will, convenience of washing as wearers wish.

According to the invention, the heating apparatus includes a soft matrix, a metal yarn and a power supply. The metal yarn is integrated with the soft matrix to construct a loop pattern by a textile process, and has a first end line and a second end line. The first end line and the second end line of the metal yarn both are detachably connected to the power supply. The power supply functions as a heating source of the heating apparatus. When the first end line and the second end line of the metal yarn is connected to power supply, the power supply supplies the metal yarn with electric energy such that the metal yarn then transfers the supplied electric energy into heat.

In an embodiment, the metal yarn substantially consists of Ni—Cr alloy fibers. In another embodiment, the metal yarn substantially consists of stainless steel fibers. Obviously, the power consumption of the heating apparatus according to the invention is lower than that of the conventional heating apparatus. Moreover, the heating apparatus of the invention can eliminate static electricity, be carried with convenience, and provide well warming efficiency.

The advantage and spirit of the invention may be understood by the following recitations together with the appended drawings.

BRIEF DESCRIPTION OF THE APPENDED DRAWINGS

DETAILED DESCRIPTION OF THE INVENTION

Figure 1:
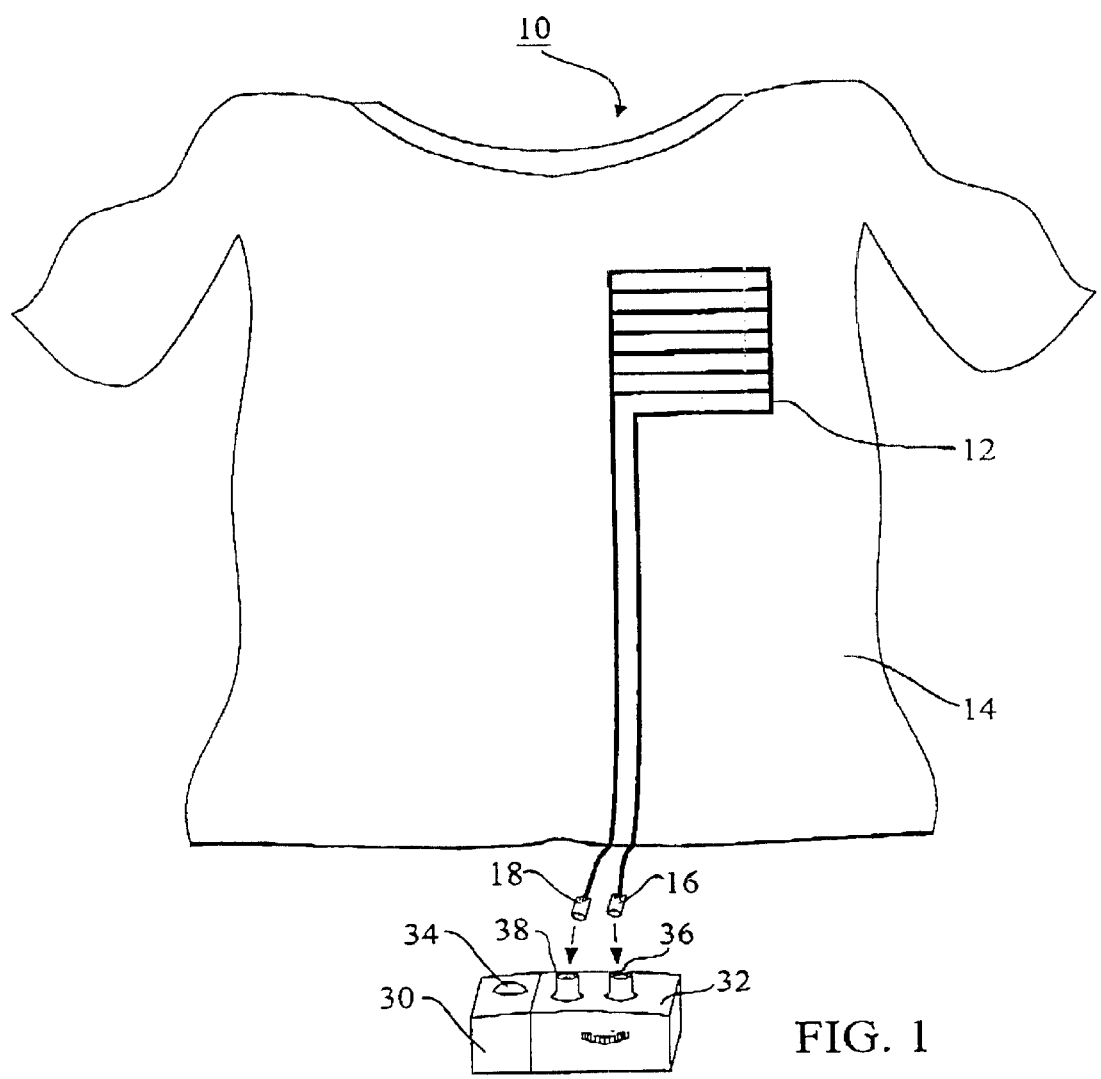
FIG. 1 illustrates schematically the hating apparatus 10 according to a first preferred embodiment of the invention.

The invention is to provide a heating apparatus which can be applied in various articles for keeping human body warm, preventing from cold weather, insulating cold air, etc., e.g., warming clothes, electric blankets, hot compress pads, and curtains for insulating cold air. Hereinafter, several preferred embodiments of the invention will be described in detail to illustrate clearly the spirit and characteristic of the invention and to reveal widespread application of the invention.
The First Preferred Embodiment of the Invention Referring to FIG. 1, a heating apparatus 10 according to the first preferred embodiment of the invention is illustrated schematically. The heating apparatus 10 includes a soft matrix 14, a metal yarn 12 and a power supply 32. The metal yarn 12 is integrated with the soft matrix 14 to construct a loop pattern by a textile process, and has a first end line 16 and a second end line 18. The first end line 16 and the second end line 18 of the metal yarn 12 are capable of detachably connecting with the first end point 36 and the second end point 38 of the power supply 32, respectively. The power supply 32 functions as an energy source of the heating apparatus 10. When the first end line 16 and the second end line 18 of the metal yarn 12 both are connected to the power supply 32, the power supply 32 supplies the metal yarn 12 with electric energy such that the metal yarn 12 then transfers the supplied electric energy into heat.

It is noted that the soft matrix 14 shown in FIG. 1 is only partially drawn to show the loop pattern constructed by the metal yarn 12, and not drawn to show the whole profile of the soft matrix 14. As for the whole profile of the soft matrix 14 and the application fields of the heating apparatus 10, it will be thoroughly described in the following paragraphs.

In one embodiment, the metal yarn 12 are spun from long metal fibers or short metal fibers, and the diameter of the metal yarn 12 is somewhat like that of a common cotton yarn. Equivalent diameter of single metal fiber in the metal yarn 12 is in a range of 1 $\mu$m to 30 $\mu$m. The materials of the metal fiber should be high corrosion-resisting, and with a proper impedance value for practical applied environment.

In one embodiment, the metal yarn 12 substantially consists of Ni—Cr alloy fibers. In another embodiment, the metal yarn 12 substantially consists of stainless steel fibers.

In one embodiment, the soft matrix 14 is a fabric, such as a piece of cloth or a ready-made garment. Using a ready-made garment as an example, the soft matrix 14 shown in FIG. 1 is a part of the ready-made garment covering the loop pattern constructed by the metal yarn 12, and the whole profile of the soft matrix 14 is the ready-made garment not completely shown in FIG. 1. If the fabric is a finished article, such as a ready-made garment, a preferred embodiment of the textile process for incorporating the metal yarn 12 and the soft matrix 14 together can be a sewing process, that is the metal yarn 12 is sewed onto the ready-made garment. If the fabric is an article not finished yet, a preferred embodiment of the textile process for incorporating the metal yarn 12 and the soft matrix 14 together can be a weaving process or a knitting process, that is the article, not finished yet, and the loop pattern are monolithically formed by the weaving process or the knitting process to finish the article.

In practical application, when the soft matrix 14 of the heating apparatus 10 according to the invention is a fabric, the heating apparatus 10 can be implemented as a wearable warming garment, an electric blanket, a warming seat cushion or a curtain for insulating cold air. Obviously, the heating apparatus 10 of the invention can be applied more widely than the conventional heating apparatus with the heavy heating coils or heating plates. The article utilizing the heating apparatus 10 of the invention is compact, lightweight, portable easily, used conveniently, and safer than those articles utilizing the conventional heating apparatuses.

In another embodiment, the soft matrix 14 is made of a rubber materials, a synthetic resin or a polymeric materials. A preferred embodiment of the textile process for incorporating the metal yarn 12 and the soft matrix 14 together can be a sewing process. In practical application, when the soft matrix 14 of the heating apparatus 10 according to the invention is one kind of rubber materials, a synthetic resin or a polymeric materials, the heating apparatus 10 can be implemented as a cushion for heating or warming, e.g., a hot compress pad, a warming seat cushion, a pedal cushion for warming feet, or a pedal cushion for melting snow on shoes.

Depending on practical article and applied environment of the heating apparatus 10 according to the invention, if the practical article of the heating apparatus 10, such as an electric blanket, is designed as being used indoor, the power supply 32 of the heating apparatus 10 can be conveniently connected to a household AC power. If the practical article of the heating apparatus 10, such as a wearable heating apparatus, is designed as being used outdoor, the power supply 32 of the heating apparatus 10 can conveniently connected to a dry battery or an rechargeable battery. The power consumption of the heating apparatus 10 according to the invention is lower than those of the conventional heating apparatuses with heating coils or heating plates. It is preferred that a power connecting with the power supply 32 is a direct current power upon consideration of safety.

In one embodiment, the first end point 36 and the second end point 38 of the power supply 32 can be clip-hold contact points or lock-up contact points for conveniently connecting with the first end line 16 and the second end line 18 of the metal yarn 12, respectively. Thereby, the combination of the metal yarn 12 and the soft matrix 14 are easily detached from the power supply 32, and then the combination of the metal yarn 12 and the soft matrix 14 can be washed. No matter what kind of the soft matrix 14 and the metal yarn 12 are, it is obvious that the heating apparatus 10 according to the invention can be designed as a washable heating apparatus without the need of additional water-proof design. That the heating apparatus is capable of being washed conveniently is very important when the heating apparatus is designed as a wearable heating apparatus or used in a dirty environment.

Also shown in FIG. 1, the heating apparatus 10 according to the first preferred embodiment of the invention further includes a temperature controller 30 and a temperature sensor 34. The temperature controller 30 is for controlling the power supply 32 to supply the metal yarn with the electric energy. The temperature sensor 34 can be set on the temperature controller 30, as shown in FIG. 1. The temperature sensor 34 can also be set on other place where need to detect temperature, and is electrically connected to the temperature controller 30. The temperature sensor 34 detects circumferential temperature and then transmits the value of the detected temperature to the temperature controller 30. The temperature controller 30 then controls the power supply 32 according to the temperature by the temperature sensor 34.

As shown in FIG. 1, the power supply 32 and the temperature controller 30 are implemented into one single controller such that the cost of the heating apparatus 10 is lowered. Of course, the power supply 32 and the temperature controller 30 can also be implemented as separate components of the heating apparatus 10 as desire.

In one embodiment, the temperature controller 30 has a microprocessor. The heating apparatus 10 gets the circumferential temperature detected by the temperature sensor 34. The microprocessor of the temperature controller 30 then automatically adjusts temperature in a predetermined temperature range according to the detected temperature. In another embodiment, the temperature controller 30 is a manual temperature controller, a user can manually control the output power of the power supply 32 to adjust the temperature to keep warm.

The Second Preferred Embodiment of the Invention

Figure 2:
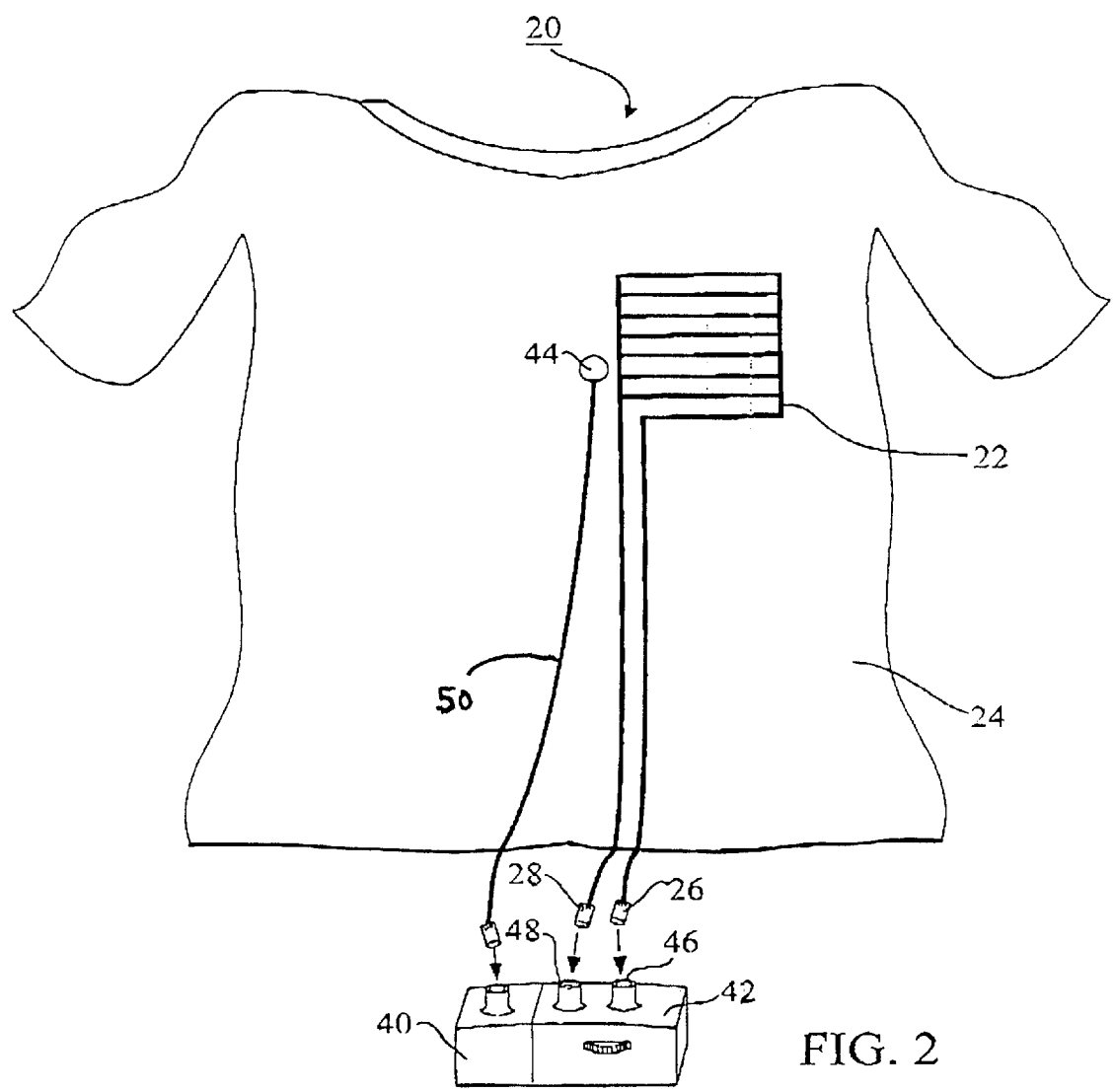
FIG. 2 illustrates schematically the hating apparatus 20 according to a second preferred embodiment of the invention.

Referring to FIG. 2, the heating apparatus 20 according to the second preferred embodiment of the invention is illustrated schematically. The heating apparatus 20 is substantially implemented as a wearable heating apparatus such as an electro-heating garment for keeping warm. The heating apparatus 20 includes a soft matrix 24, a metal yarn 22, a power supply 42, a temperature controller 40, and a temperature sensor 44. A preferred embodiment of the soft matrix 24 is a fabric.

The metal yarn 22 is integrated with the soft matrix 24 to construct a loop pattern by a textile process, and has a first end line 26 and a second end line 28. The first end line 26 and the second end line 28 of the metal yarn 22 are capable of detachably connecting with the first end point 46 and the second end point 48 of the power supply 42, respectively. The power supply 42 functions as an energy source of the heating apparatus 20. When the first end line 26 and the second end line 28 of the metal yarn 22 both are connected to the power supply 42, the power supply 42 supplies the metal yearn 22 with electric energy such that the metal yarn 22 transfers the supplied electric energy into heat which consequently provides the heat source of the heating apparatus 20.

As shown in FIG. 2, the power supply 42 and the temperature controller 40 are implemented into one single controller such that the cost of the heating apparatus 20 is lowered. Alternatively, the power supply 32 and the temperature controller 30 can be implemented as separate components of the heating apparatus 10.

For the design of the wearable heating apparatus, as shown in FIG. 2, the temperature sensor 44 is set on a proper place of the soft matrix 24 where it is close to the wearer's body needed to keep warm. The temperature sensor 44 is detachably connected to the temperature controller 40 via a conducting wire 50. It is preferred that the temperature sensor 44 detects the temperature of a "microclimate" of the wearer. The so-called microclimate is an atmosphere existing between the wearable heating apparatus and the wearer. The temperature sensor 44 then transmits the detected temperature to the temperature controller 40 via the conducting line 50. The temperature controller 40 then controls the power supply 42 according to the temperature of the microclimate detected by the temperature sensor 44. This can provide well warming efficiency and save the power consumption. The temperature sensor 44 has to be a water-proof component or be processed with a water-proof treatment.

For the wearable heating apparatus, the soft matrix 24 can be implemented as a common ready-made garment, gloves, socks, etc. The power supply 42 and the temperature controller 40 is integrated into one single controller which can be easily worn on the waist. This makes the wearing of the wearable heating apparatus and the attaching/detaching between the soft matrix 24 and the power supply 42 easy. The metal yarn 22 can be sew on a place that would near the physical region needed to keep warm as wearer wish, e.g., the wear's belly, back, heart region, even or whole body. Therefore, the wearable heating apparatus according to the invention gives practical warming efficiency and is easy for being carried. It is emphasized that the significant feature of the wearable heating apparatus of the invention is elimination of heavy and non-wearable heating apparatuses with heavy heating coils or heating plates, i.e., heaviness and non-washable heating components in the conventional heating apparatuses. In addition, the wearable heating apparatus of the invention uses the metal yarn formed of metal fibers can also provide the function for eliminating static electricity and protecting from electromagnetic interference.

On summary, the invention provides a heating apparatus utilizing a metal yarn instead of heavy heating coils or heating plates. Differing from the conventional heating apparatus, the heating apparatus of the invention consumes a small quantity of power, and is light-weight and compact. In addition, the heating apparatus of the invention is washable due to use of high corrosion-resistant metal fibers.

While the invention has been described in several preferred embodiments, it is understood that the words which have been used are words of description rather than words of limitation and that changes within the purview of the appended claims may be made without departing from the scope and spirit of the invention in its broader aspect.

What is claimed is:

1. A heating apparatus, comprising:
    a soft matrix;
    a metal yarn being integrated with the soft matrix to construct a loop pattern by a textile process, and having a first end line and a second end line; and
    a power supply to which the first end line and the second end line of the metal yarn being detachably connected;
    wherein when the first end line and the second end line of the metal yarn both are connected to power supply, the power supply supplies the metal yarn with electric energy such that the metal yarn transfers the supplied electric energy into heat.

2. The heating apparatus according to claim 1, wherein the metal yarn substantially consists of Ni—Cr alloy fibers.

3. The heating apparatus according to claim 1, wherein the metal yarn substantially consists of stainless steel fibers.

4. The heating apparatus according to claim 2, wherein the soft matrix is a fabric, and the textile process is one selected from the group consisting of a sewing process, a weaving process and a knitting process.

5. The heating apparatus according to claim 4, further comprising a temperature controller for controlling the power supply to supply the metal yarn with the electric energy.

6. The heating apparatus according to claim 5, further comprising a temperature sensor electrically connected to the temperature controller, wherein the temperature controller controls the power supply in accordance with temperature measured by the temperature sensor.

7. The heating apparatus according to claim 2, wherein the soft matrix is made of one selected from the group consisting of a rubber material, a synthetic resin and a polymeric material, and the textile process is a sewing process.

8. The heating apparatus according to claim 7, further comprising a temperature sensor for controlling the power supply to supply the metal yarn with electric energy.

9. The heating apparatus according to claim 8, further comprising a temperature sensor connected to the temperature controller, wherein the temperature controller controls the power supply in accordance with temperature measured by the temperature sensor.

10. A wearable heating apparatus, comprising:
   a temperature controller;
   a power supply, controller by the temperature controller, for supplying with electric energy;
   a fabric; and
   a metal yarn being integrated with the soft matrix to construct a loop pattern by a textile process, and the metal yarn having a first end line and a second end line detachable connected to the power supply, wherein when the first end line and the second end line of the metal yarn both are connected to the power supply, the power supply, controlled by the temperature controller, supplies the metal yarn with electric energy such that the metal yarn transfers the supplied electric energy into heat.

11. The wearable heating apparatus according to claim 10, wherein the textile process is one selected from the group consisting of a sewing process, a weaving process and a knitting process.

12. The wearable heating apparatus according to claim 11, further comprising a temperature sensor electrically connected to the temperature controller, wherein the temperature controller controls the power supply in accordance with temperature measured by the temperature sensor.

13. The wearable heating apparatus according to claim 12, wherein the metal yarn substantially consists of Ni—Cr alloy fibers.

14. The wearable heating apparatus according to claim 13, the temperature sensor is set on the fabric, and is detachably and electrically connected to the temperature controller.

15. The wearable heating apparatus according to claim 12, wherein the metal yarn substantially consists of stainless steel fibers.

* * * * *